United States Patent [19]

Alpegiani et al.

[11] Patent Number: 5,200,403
[45] Date of Patent: Apr. 6, 1993

[54] INHIBITION OF β LACTAMASE WITH 6 β-(SUBSTITUTED METHYL)-PENICILLANIC ACID DERIVATIVES

[75] Inventors: Marco Alpegiani, Milan, Italy; Stephen Hanessian, Beaconsfield, Canada; Giuseppe Meinardi; Ettore Perrone, both of Milan, Italy

[73] Assignee: Farmitalia Carlo Erba S.r.l., Milan, Italy

[21] Appl. No.: 734,559

[22] Filed: Jul. 23, 1991

Related U.S. Application Data

[62] Division of Ser. No. 217,713, Jul. 11, 1988, abandoned.

[51] Int. Cl.$^5$ .............................................. A61K 31/43
[52] U.S. Cl. ................................................... 514/195
[58] Field of Search ........................................ 514/195

[56] References Cited

U.S. PATENT DOCUMENTS 4,656,263 4/1987 Kellogg ................................ 540/310
4,847,247 7/1989 Thompson et al. ................. 514/194

OTHER PUBLICATIONS

Tetrahydron Letters, vol. 27, pp. 4857–4860, 1986.

Primary Examiner—Leonard Schenkman
Attorney, Agent, or Firm—Oblon, Spivak, McClelland, Maier & Neustadt

[57] ABSTRACT

Compounds of the formula I

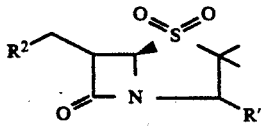

wherein R' is a free or esterified carboxy group or a carboxylate anion and R$^2$ is an organic group have beta-lactamase inhibition activity. A process for the preparation of the same and pharmaceutical compositions containing these compounds are provided.

3 Claims, No Drawings

INHIBITION OF β LACTAMASE WITH 6 β-(SUBSTITUTED METHYL)-PENICILLANIC ACID DERIVATIVES

This is a division of application Ser. No. 07/217,713, filed on Jul. 11, 1988, abandoned.

BACKGROUND OF THE INVENTION

1. Field of the Invention

This invention relates to 6α- and 6β-(substituted methyl)-penicillanic acid derivatives, and pharmaceutical and veterinary compositions containing the same. The present invention also relates to methods for the preparation of these compounds and their use as beta-lactamase inhibitors, and intermediates thereof.

2. Description of the Background

Although various antibiotics such as penicillins and cephalosporins, for example, are known to be effective against certain types of bacteria, many bacteria have resistance to such β-lactam antibiotics by virtue of their production of enzymes which destroy the β-lactam antibiotic, i.e., β-lactamase.

Thus, a need continues to exist for antibiotics or compositions containing the same which are resistant to β-lactamase enzymes.

SUMMARY OF THE INVENTION

Accordingly, it is an object of the present invention to provide compounds which are useful as β-lactamase inhibitors.

It is also an object of the present invention to provide compositions containing a mixture of one or more β-lactam antibiotics with one or more of the present compounds having β-lactamase inhibiting activity.

Moreover, it is also an object of this invention to provide pharmaceutical and veterinary compositions containing one or more of the present compounds.

Further, it is also an object of this reference to provide methods for the preparation of the present compounds and intermediates for the present compounds.

Accordingly, these and other objects are provided by compounds of the formula (I)

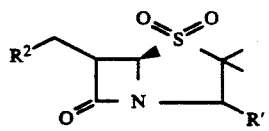

(I)

wherein:
R' represents a free or esterified carboxy group or a carboxylate anion; and
R² represents
 a) an unsubstituted or substituted vinyl group of the formula

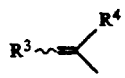

in which each of R³ and R⁴ independently represents a hydrogen atom or a lower alkyl, aryl, aralkyl or protected hydroxy group
b) an unsubstituted or substituted oxiranyl group of the formula

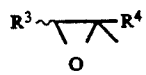

in which R³ and R⁴ are as defined above;
c) a free or esterified carboxy group or a carboxylate anion;
d) a formyl or acetyl group or a hydroxyimino or alkoxyimino derivative of such a group;
e) a cyano, carbamoyl or amidino group;
f) a group of the formula —CH₂R⁵ in which R⁵ represents
 i) a hydrogen or halogen atom or an azido group,
 ii) an optionally substituted alkyl, alkenyl or alkynyl group, each of which has up to 4 carbon atoms,
 iii) a free or protected hydroxy group,
 iv) an optionally substituted alkoxy having up to 4 carbon atoms or an optionally substituted acyloxy group,
 v) a group of the formula SR or NHR, wherein R represents a hydrogen atom, an unsubstituted or substituted alkyl or alkanoyl group, each of which has up to 4 carbon atoms, or a mercapto or amino protecting group,
 vi) an optionally substituted alkylsulphinyl or alkylsulphonyl group, each of which has up to 4 carbon atoms,
 vii) an optionally substituted heterocyclylthio group,
 viii) an optionally substituted imido group,
 ix) a quaternary ammonium group, or
 x) an unsubstituted or substituted carbamoyloxy group of the formula R³HN.COO— in which R³ is as defined above or an unsubstituted or substituted ureido group of the formula R³HN.CO.NH— in which R³ is as defined above, or the pharmaceutical and veternarily acceptable salts thereof.

DESCRIPTION OF THE PREFERRED EMBODIMENTS

The present invention provides compounds having the formula I

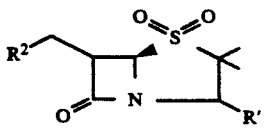

(I)

wherein:
R' represents a free or esterified carboxy group or a carboxylate anion; and
R² represents
 a) an unsubstituted or substituted vinyl group of the formula

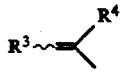

independently represents a hydrogen atom or a lower alkyl, aryl, aralkyl or protected hydroxy group b) an unsubstituted or substituted oxiranyl group of the general formula

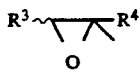

in which $R^3$ and $R^4$ are as defined above;
c) a free or esterified carboxy group or a carboxylate anion;
d) a formyl or acetyl group or a hydroxyimino or alkoxyimino derivative of such a group;
e) a cyano, carbamoyl or amidino group;
f) a group of the formula —$CH_2R^5$ in which $R^5$ represents
  i) a hydrogen or halogen atom or an azido group,
  ii) an optionally substituted alkyl, alkenyl or alkynyl group, each of which has up to 4 carbon atoms,
  iii) a free or protected hydroxy group,
  iv) an optionally substituted alkoxy having up to 4 carbon atoms or an optionally substituted acyloxy group,
  v) a group of the formula SR or NHR, wherein R represents a hydrogen atom, an unsubstituted or substituted alkyl or alkanoyl group, each of which has up to 4 carbon atoms, or a mercapto or amino protecting group,
  vi) an optionally substituted alkylsulphinyl or alkylsulphonyl group, each of which has up to 4 carbon atoms,
  vii) an optionally substituted heterocyclylthio group,
  viii) an optionally substituted imido group,
  ix) a quaternary ammonium group, or
  x) an unsubstituted or substituted carbamoyloxy group of the general formula $R^3HN.COO$— in which $R^3$ is as defined above or an unsubstituted or substituted ureido group of the formula $R^3HN.CO.NH$— in which $R^3$ is as defined above, and further provides pharmaceutical or veternarily acceptable salts thereof.

The compounds provided by the present invention have a (3S, 5R, 6S) or (3S, 5R,6R) configuration, the substituted methyl group at position 6 being α or β oriented.

The pharmaceutically or veternarily acceptable salts of the compounds of the invention include both salts with inorganic bases such as alkali or alkaline earth metal hydroxides, in particular sodium and potassium hydroxides, and salts with organic bases such as triethylamine, pyridine, benzylamine and collidine. Salts with aminoacids such as lysine and procaine are also included, as are inner salts, i.e. zwitterions.

When R' represents an esterified carboxy group it is a group COO-linked through the oxygen atom to an organic radical, such as a $C_1$–$C_6$ alkyl group, for instance methyl, ethyl or t-butyl; a substituted $C_1$–$C_6$ alkyl group, for example 2,2,2-trichloroethyl, trimethylsilylethyl or α-phenoxyethyl; a $C_2$–$C_6$ alkenyl group, for example allyl; an optionally substituted aryl group, for example phenyl or p-nitrophenyl; an optionally substituted aryl-$C_1$–$C_6$ alkyl group, for example benzyl, p-nitrobenzyl or p-methoxybenzyl; or groups such as benzhydryl, o-nitrobenzhydryl, acetonyl, phenacyl, trimethylsilyl, diphenyl-t-butylsilyl, and dimethyl-t-butylsilyl. The definition of R' as an esterified carboxy group includes also a carboxy group esterified with any residue which is known to be hydrolysed "in vivo", such as acetoxymethyl, 1-acetoxyethyl, pivaloyloxymethyl, 3-phthalidyl, ethoxycarbonyloxyethyl; ethoxycarbonyloxymethyl, 4-crotonolactonyl, gamma-butyrolactonyl and 5-methyl-2-oxo-1,3-dioxolen-4-yl)-methyl.

The lower alkyl groups referred to contain 1 to 4 carbon atoms.

The term "aryl" refers to phenyl substituted by one or more substituent groups. Such aryl groups represented by $R^3$ or $R^4$ can be for example phenyl, 4-fluorophenyl, 2-methoxyphenyl, 3-aminophenyl and 2-hydroxypehnyl. The term "aralkyl" encompasses aryl substituted lower alkyl groups such as benzyl, phenethyl and p-fluorobenzyl. When $R^5$ is a protected hydroxy, mercapto or amino group, it is preferably protected with silyl groups, in particular trimethylsilyl, t-butyldimethylsilyl or t-butyldiphenylsilyl, or as a carbonate with groups such as allyloxycarbonyl, p-nitrobenzyloxycarbonyl, trichloroethoxycarbonyl and p-methoxybenzyloxycarbonyl, or with groups such as pyranyl, trifluoroacetyl, triphenylmethyl and t-butyl.

A heterocyclylthio group is a group of the formula:

wherein Het represents a saturated or unsaturated, monocyclic or bicyclic ring, containing from 1 to 5 heteroatoms selected from oxygen, nitrogen and sulphur.

An imido group is a five or six-membered cyclic imido group

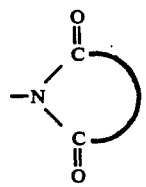

optionally incorporating, in addition to the imido nitrogen, one or two heteroatoms selected from nitrogen, oxygen and sulphur, said cyclic imido group being optionally fused with a benzene or pyridine ring.

A quaternary ammonium group is a group

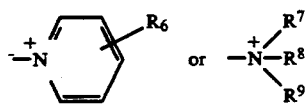

wherein
$R^6$ represents an alkyl group having up to 3 carbon atoms or a hydroxy, amino, carboxy, methoxy, methylthio or carbamoyl group
and each of $R^7$, $R^8$ and $R^9$ independently represents an optionally substituted alkyl, aralkyl or aryl radical.

Preferred substituents for the aryl and aralkyl groups under (a) and (b),
the alkyl groups under (a), (b) and (fii),
the alkenyl and alkynyl groups under (fii),
the alkoxy, alkylthio, alkylamino,
alkylsulphinyl and alkylsulphonyl groups under (d), (fiv), (fv) and (fvi),
the acyloxy, acylthio, acylamino under (fiv) and (fv), the heterocyclylthio group under (fvii),
the imido group under (fviii),
and the $R^7$, $R^8$ and $R^9$ radicals of the ammonium group as defined above are (a') halogen
(b') hydroxy
(c') $(C_1-C_4)$ alkoxy
(d') $(C_1-C_4)$ alkylthio
(e') amino, optionally mono- or di-substituted with $(C_1-C_4)$ alkyl groups
(f') sulfo
(g') free or esterified carboxy
(h') carbamoyl
(k') carbamoyloxy
(l') formamido or acetamido
(n') $(C_1-C_4)$ alkanoyl group
(p') nitro
(q') $(C_1-C_4)$ alkyl group In the present specification, the term halogen encompasses fluorine, chlorine, bromine or iodine.

A $(C_1-C_4)$ alkyl group is, preferably, methyl or ethyl.

A $(C_1-C_4)$ alkynyl group is, preferably, ethynyl or propynyl.

A $(C_1-C_4)$ alkoxy group is, preferably, methoxy or ethoxy.

A $(C_1-C_4)$ alkanoyl group is, preferably, formyl or acetyl.

R' represents sodium or potassium carboxylate (COONa, COOK), a free carboxy group, acetoxymethoxycarbonyl, pivaloyloxymethoxycarbonyl or 1-(ethoxycarbonyloxy)ethoxycarbonyl or, when $R^5$ is a quaternary ammonium cation as defined above, a carboxylate anion COO$^-$; and $R^2$ represents (a'') a group

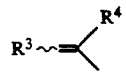

in which $R^3$ and $R^4$ independently represent a hydrogen atom or a methyl, benzyl or a phenyl group (b'') a group

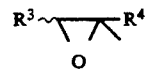

in which $R^3$ and $R^4$ are as defined in (a'')

(c'') a carboxy group, a sodium or potassium carboxylate, a methoxycarbonyl, acetoxymethoxycarbonyl or pivaloyloxymethoxy carbonyl group (d'') a formyl, acetyl, hydroxyiminoformyl or methoxyiminoformyl group (e'') a cyano or carbamoyl group (f'') a —CH$_2$R$^5$ group wherein $R^5$ is either
 (i) a hydrogen or halogen atom,
 (ii) a methyl, vinyl or ethynyl group
 (iii) a hydroxy group
 (iv) a methoxy, ethoxy, formyloxy or acetoxy group
 (v) a mercapto, methylthio, ethylthio, acetylthio, amino, methylamino, dimethylamino, formamido or acetamido group
 (vi) a methylsulphinyl or methylsulphonyl group
 (vii) a 6-methoxy-2-pyrazinylthio, 4,5-dihydro-4-methyl-5-oxo-6-hydroxy-1,2,4-triazin-3-ylthio, 2,5-dihydro-2-methyl-5-oxo-6-hydroxy-1,2,4-triazin-3-ylthio, 1-sulphomethyl-5-tetrazolylthio, 1H-5-tetrazolylthio, 1-carboxymethyl-5-tetrazolylthio, 1-methyl-5-tetrazolylthio, 1-($\beta$ dimethylaminoethyl)-5-tetrazolylthio, 2-carboxymethylthio-1,3,4-thiadiazol-5-ylthio, tetrazolo[1,5-b]pyridazin-6-ylthio, 8-carboxytetrazolo[1,5-b]pyridazin-6-ylthio or 8-amino-tetrazolo[1,5-b]pyridazin-6-ylthio group, (viii) a succinimido, phthalimido, 2,5-dioxo-3-amino-1-pyrrolidinyl, 2,4-dioxo-1,3-oxazolidin-3-yl, 2,4-dioxo-1,3-thiazolidin-3-yl, 2,4-dioxo-1,3-imidazolidin-3-yl, 2,4-dioxo-1,2,3,4-tetrahydropyrimidin-3-yl-uracyl, 5,6-dihydro-7H- 5,7-dioxo-pyrrolo[3,4-b]pyridin-6-yl (pyridin-2,3-carboxyimido) or 1,2-dihydro-3H-1,3-dioxo-pyrrolo [3,4-c]pyridin-2-yl group (pyridin-3,4-carboxyimido), (ix) a trimethylammonium, triethylammonium, N-methylpyrrolidinium, N-methylpiperidinium, N-methylmorpholinium, quinuclidinium, pyridinium, 4-methoxy-pyridinium 4-dimethylamino-pyridinium 3-carbamoyl-pyridinium, 4-carbamoyl-pyridinium, 3-carboxymethyl-pyridinium, 5,6-dihydro-7H-cyclopenta(b)pyridinium, quinolinium or isoquinolinium group, (x) an unsubstituted or substituted carbamoyloxy group of the formula $R^3$HN.COO— in which $R^3$ is as defined in (a'') above or an unsubstituted or substituted ureido group of the formula $R^3$HN.CO.NH— in which $R^3$ is as defined in (a'') above.

Specific examples of preferred compounds of the invention are the acids listed in the following table, either as such or as the sodium, potassium or inner salts or "in vivo" hydrolyzed esters thereof.

TABLE I

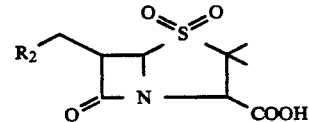

| Compound | C-6 configuration | $R^2$ |
|---|---|---|
| 1 | S | vinyl |
| 2 | S | 1-propenyl |
| 3 | S | carboxy |
| 4 | S | formyl |
| 5 | S | carbamoyl |
| 6 | S | hydroxymethyl |
| 7 | S | fluoromethyl |
| 8 | S | ethyl |
| 9 | S | carbamoyloxymethyl |
| 10 | S | 1-methyl-5-tetrazolylthiomethyl |
| 11 | S | succinimidomethyl |
| 12 | S | pyridiniummethyl |
| 13 | S | styryl |
| 14 | S | phenethyl |
| 15 | S | oxiranyl |
| 16 | S | 3-phenyl-2-oxiranyl |
| 17 | S | 3-methyl-2-oxiranyl |
| 18 | R | vinyl |
| 19 | R | 1-propenyl |
| 20 | R | allyl |
| 21 | R | oxiranyl |
| 22 | R | formyl |
| 23 | R | methoxyiminomethyl |
| 24 | R | carboxy |
| 25 | R | methoxycarbonyl |
| 26 | R | carbamoyl |
| 27 | R | cyano |
| 28 | R | methyl |
| 29 | R | fluoromethyl |
| 30 | R | chloromethyl |
| 31 | R | bromomethyl |

TABLE I-continued

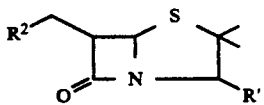

| Compound | C-6 configuration | R² |
|---|---|---|
| 32 | R | iodomethyl |
| 33 | R | ethyl |
| 34 | R | hydroxymethyl |
| 35 | R | methoxymethyl |
| 36 | R | formyloxymethyl |
| 37 | R | acetoxymethyl |
| 38 | R | mercaptomethyl |
| 39 | R | aminomethyl |
| 40 | R | methylthiomethyl |
| 41 | R | methylaminomethyl |
| 42 | R | dimethylaminomethyl |
| 43 | R | acetamidomethyl |
| 44 | R | methylsulphonylmethyl |
| 45 | R | 1-methyl-5-tetrazolylthiomethyl |
| 46 | R | 6-methoxy-2-pyrazinylthiomethyl |
| 47 | R | 1H-5-tetrazolylthiomethyl |
| 48 | R | 1-(β-dimethylaminoethyl)-5-tetrazolylthiomethyl |
| 49 | R | phthalimidomethyl |
| 50 | R | 2,5-dioxo-3-amino-1-pyrrolidinyl-methyl |
| 51 | R | 2,4-dioxo-1,3-thiazolidin-3-ylmethyl |
| 52 | R | trimethylammonium |
| 53 | R | triethylammonium |
| 54 | R | N-methyl-pyrrolidinium |
| 55 | R | N-methyl-morpholinium |
| 56 | R | N-methyl-piperidinium |
| 57 | R | pyridinium |
| 58 | R | 3-carboxymethyl-pyridinium |
| 59 | R | styryl |
| 60 | R | 3-phenyl-2-oxiranyl |
| 61 | R | 3-methyl-2-oxiranyl |

For convenience, compounds I wherein R² has any of the values listed in (a) above will be referred to as compounds I(a); compounds I(b), I(c), I(d), I(e) and I(f) will likewise be understood to be the compounds I in which R² has any of the values listed above in (b), (c), (d), (e) and (f) respectively. Further, compounds I' will be the 1,1-dideoxy equivalents of compounds I, having the formula:

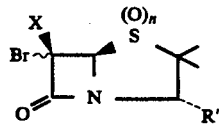

wherein R² and R' are as above defined; and compounds I'(a) to I'(f) will be understood to be the compounds I' in which R² has any of the values listed above in (a) to (f) respectively.

The invention also provides a process for the preparation of the compound I as above defined, the process comprising reacting a compound of the general formula II:

wherein X represents a hydrogen or bromine atom, n is 0 or 2 and R' is as above defined with a compound of the general formula III:

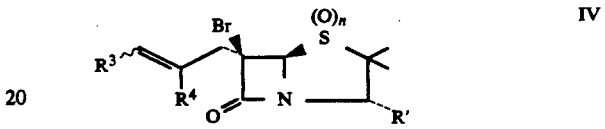

wherein $R^{10}$ represents an alkyl group having from 1 to 8 carbon atoms or an aryl group and $R^3$ and $R^4$ are as above defined;

and if X represents a bromine atom, reacting the resultant compound of the general formula IV:

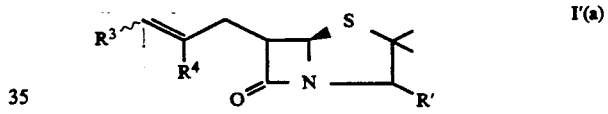

wherein $R^3$, $R^4$, R' and n are as above defined with a tin hydride of the general formula V:

$$H\ Sn\ (R^{10})_3$$

wherein $R^{10}$ is as above defined;

thereby obtaining (when n=0) a compound of the formula I'(a):

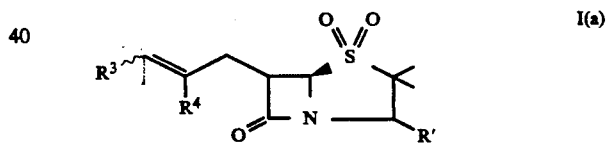

or (when n=2) a compound of the formula I(a):

the compound I'(a) or I(a) being in the 6R configuration if X represents a bromine atom and in the 6S configuration if X represents a hydrogen atom;

and, if n=0 and a compound of the formula I(a) is desired, oxidising the compound of the formula I'(a), and, if n=2 and a compound of the formula I(b-f) is desired, converting the 6-substituent in the compound I(a) to the desired 6-substituent, and, if n=0 and a compound of the formula I(b-f) is desired, either proceeding according to the last two preceding steps, or converting the 6-substituent in the compound I'(a) to the desired 6-substituent and oxidising the resultant compound of the formula I'(b-f).

In compounds III and V, $R^{10}$ preferably represents a methyl, ethyl, n-propyl, n-butyl, s-butyl, n-pentyl or phenyl group.

The reaction between compounds II and III may be carried out by heating equimolar mixtures thereof, or mixtures containing an excess of the compound III, in an inert organic solvent such as benzene, toluene or xylene, preferably under argon or nitrogen, in the presence of a catalytic amount of a radical initiator such as 2,2'-azo-bis(2-methylpropionitrile), hereinafter known as AIBN. The reaction proceeds in a very efficient way with a remarkable degree of stereocontrol, the functionally versatile allyl group being introduced at C-6 exclusively from the α-face. When X represents a hydrogen atom, this reaction therefore leads directly to compounds I(a) or I'(a) in the 6S configuration. When X represents a bromine atom, the reaction leads to a compound IV, which is further reacted with a compound V under similar conditions. In this case, it is the hydrogen atom which is introduced exclusively from the α-face, so that the reaction leads to compounds I(a) or I'(a) in the 6R configuration. The yields are typically greater than 80% and the reaction products may easily be purified by flash chromatography.

The oxidation of compounds I' to compounds I may be carried out using any of the oxidizing agents known to be capable of transforming a sulphide into a sulphone. Preferred oxidizing agents include organic peracids such as m-chloroperbenzoic acid, perphthalic acid, performic acid, permaleic acid or peracetic acid. Preferred oxidizing agents also include inorganic oxidizing agents such as potassium permanganate, sodium metaperiodate and potassium persulphate. The reaction may be carried out in a solvent such as dichloromethane, chloroform, benzene, tetrahydrofuran, acetone, ethanol, water or a mixture of two or more thereof, at a temperature of from $-20°$ C. to $+50°$ C.

The conversion of the 6-substituent in the compound I(a) or I'(a) may be effected by any known methods exploiting the allyl function. For instance, oxidation of the double bond in the 6-substituent of a compound I(a) or I'(a), using a peracid such as m-chloroperbenzoic acid, leads to the corresponding compounds I(b) . Ozonolysis of the same double bond will lead to compounds I or I' in which the 6-substituent is $R^4$—CO—CH$_2$, corresponding to $R^2$ being a formyl group when $R^4$ represents a hydrogen atom. Oxidation of the formyl group leads to compounds in which $R^4$ represents a carboxy group, while reduction using a mild reducing agent such as sodium cyanoborohydride, sodium borohydride or potassium selectride gives the corresponding alcohols, compounds I'(f), $R^5=OH$ and I'(f), $R^5=OH$.

The compounds I'(f), $R^5=OH$ and I(f), $R^5=OH$ may be converted into other compounds I(f) and I'(f) by known reactions of primary alcohol groups. Amongst these, a few are now given by way of non-limiting example.

1) a compound I(f) or I'(f) wherein R5 is acyloxy may be obtained by reaction with an acyl chloride or anhydride, preferably in the presence of a base, or with a carboxylic acid under Mitsunobu conditions, i.e. in the presence of a phosphine, e.g. triphenylphosphine and an azodicarboxylate, e.g. diethyl azodicarboxylate (see, for example, *Synthesis* 1981, 1);

2) a compound I(f) or I'(f) wherein R5 is a carbamoyloxy may be obtained by reaction with an isocyanate, such as trichloroacetyl isocyanate or chlorosulphonyl isocyanate, followed by conventional removal of the trichloroacetyl or chlorosulphonyl groups;

3) a compound I(f) or I'(f) wherein $R^5$ is an optionally substituted heterocyclylthio group may be obtained by reaction with the corresponding heterocyclyl-thiol, or with a salt thereof with an organic or inorganic base; said reaction being carried out either under Mitsunobu conditions, or by first activating the hydroxy group into a nucleofugous leaving group, such as a mesylate or a tosylate;

4) a compound I(f) or I'(f) wherein $R^5$ is an imido group may be obtained by reaction with the corresponding imide, preferably carried out under Mitsunobu conditions;

5) a compound I(f) or I'(f) wherein $R^5$ is a quaternary ammonium group may be obtained by converting the hydroxy group into a nucleofugous leaving group, preferably a trifluoromethylsulphonate, which is then displaced, preferably in situ, by the parent amine.

Furthermore, other compounds I(f) or I'(f) may be prepared from compounds I(f), $R^5$-halo or I'(f), $R^5$=halo by reaction with an appropriate nucleophile, e.g. a $C_1$–$C_4$ carboxylate, the salt of an heterocyclicthiol or of an imide, or a tertiary or aromatic amine. The general conditions of such reactions, as well as of the reactions listed above under 1)–5), are known to those skilled in the art.

Compounds of the general formulae II, III and V are known compounds or may be prepared via a variety of known methods or variations thereof.

The compounds according to the invention are useful as inhibitors of β-lactamase enzymes, increasing the range of antibacterial effectiveness of penicillins, cephalosporins, monobactams and nocardicins, by their effectiveness against those microorganisms which are resistant to the β-lactam antibiotics by their production of enzymes which would otherwise destroy the β-lactam antibiotic.

The compounds of the invention are preferably used in combination with penicillins, cephalosporins or monolactams of established clinical utility, for instance ampicillin, amoxicillin, azocillin; bacampicillin, pivampicillin, carbenicillin, mecillinam, talampicillin, penicillin G; penicillin V, cefaclor, cefadroxyl, cefuroxime, ceftriaxone, caphalotin, cefotiam, cephaloridin, cephalexin, cephaloglycin, azthreonam and the pharmaceutically acceptable salts thereof. The compounds of the invention can also be administered separately.

Accordingly, the invention further provides a pharmaceutical composition comprising a compound of the formula I as above defined in admixture with a pharmaceutically acceptable diluent or carrier and, optionally, with another β-lactam antibiotic.

The pharmaceutical composition may be prepared either for parenteral or oral use. If another β-lactam antibiotic is included, it is preferably in an amount of 10% to 90% by weight of the total active ingredient, which should be present in an amount sufficient successfully to treat a bacterial infection in mammals in a single or multiple dose. Said compositions are effective in treating infections caused by Gram-positive and -negative bacteria.

The compounds of formula I, especially in the form of enzymatically labile esters, such as acetoxymethyl esters, when administered orally in combination with orally administered β-lactam antibiotics, increase the therapeutic effectiveness of said antibiotics. Some of the compounds of formula I were found comparable or even superior to clavulanic acid and sulbactam in the inhibition of many β-lactamases. For example, the inhibition power of compound No. 18 (Table 1), namely 6β-allyl-penicillanic acid 1,1-dioxide (code-named FCE 25064) was compared with that of sulbactam against the β-lactamase from Escherichia Coli TEM (type Ia according to M.H. RICHMOND and R.B. SYKES, "The β-lactamase of Gram-negative bacteria and their possible physiological role," Advances in Microbial Physiology 9, 31–85, 1973). The enzyme was incubated with a concentration of $10^{-4}$ M cephaloridine and $10^{-4}$ M FCE 25064. The residual enzyme activity of FCE 25064 (calculated by subtracting the enzyme activity of the inhibited reaction from the values of the uninhibited reaction) after 1, 2 and 4 minutes was respectively 14.7%, 9.0% and 8.1%, while Sulbactam under the same conditions gave residual enzyme activity values of 89.5%, 88.0% and 80.5% respectively.

The following Examples are provided in order to illustrate the present invention, but are not intended to limit the same.

EXAMPLE 1

Methyl 6-α-Allyl Penicillanate 2 g (6.04 mmol) of Allyltributyltin and a catalytic amount (100 mg) of AIBN were added to a solution of 1.2 g (4.08 mmol) methyl 6-α-bromo-2,2-dimethylpenam-3-carboxylate in 50 ml of benzene. The resulting mixture was refluxed under argon for 5 hours. Flash chromatography (230–400 mesh $SiO_2$, n-hexane then n-hexane/ethyl acetate mixtures as eluants) of the crude mixture allowed the isolation of the title compound as a colorless oil (905 mg; 87%).

| |
|---|
| $[\alpha]_D$ +237°(c 4.1 $CHCl_3$) |
| IR(film)1780, 1755, 1645 $c^{-1}$ |
| MH+ 256, (MH+ —$C_5H_6O$)174 |
| NMR(400 MHz, $CDCl_3$) |
| δ: 1.46(3H, s) |
| 1.63(3H, s) |
| 2.50(2H, m) |
| 3.39(1H, m) |
| 3.76(3H, s) |
| 5.06(1H, d, J=1.6Hz) |
| 5.11–5.16(2H, m) |
| 5.85(1H, m) |

EXAMPLE 2

Allyl 6-α-Allyl Penicillanate

Starting from allyl 6-α-bromo penicillanate and following the same procedure as described for the analogous penicillin methyl ester (EXAMPLE 1), the title product was obtained as colorless oil (85%).

| |
|---|
| $[\alpha]_D$ +213°(c 2.7 $CHCl_3$) |
| IR(film)3080, 1775, 1745 $c^{-1}$ |
| NMR(400 MHz, $CDCl_3$) |
| δ: 1.47(3H, s) |
| 1.64(3H, s) |
| 2.53–2.67(2H, m) |
| 3.87(1H, m) |
| 4.49(1H, s) |
| 4.65(2H, d, J=5.8Hz) |
| 5.06(1H, d, J=1.5Hz) |
| 5.14(1H, s) |
| 5.15(1H, dd, J=1.3 and 8.4Hz) |
| 5.29(1H, dd, J=1.3 and 8.3Hz) |
| 5.38(1H, dd, J=1.4 and 17.1Hz) |
| 5.79–5.97(2H, m) |

EXAMPLE 3 p-Methoxybenzyl 6-α-Allyl penicillanate

Starting from p-methoxybenzyl 6-α-bromopenicillanate and following a procedure similar to that described in EXAMPLE 1, the title product was obtained as colorless oil (81% yield).

| |
|---|
| IR($CHCl_3$)1765, 1745 $cm^{-1}$ |
| NMR($CDCl_3$, 90 MHz) |
| δ: 1.34(3H, s) |
| 1.58(3H, s) |
| 2.57(2H, m) |
| 3.35(1H, m) |
| 3.78(3H, s) |
| 4.44(1H, s) |
| 5.02(1H, d, J<2Hz) |
| 5.1–5.4(2H, m) |
| 5.11(2H, s) |
| 5.6–6.0(1H, m) |
| 6.87(2H, d, J=8.5Hz) |
| 7.30(2H, d, J=8.5Hz) |

EXAMPLE 4

2-Trimethylsilylethyl 6-α-Allyl Penicillanate

Starting from 2-trimethylsilylethyl 6-α-bromo penicillanate and following a methodology similar to that described in EXAMPLE 1, the title compound was obtained as colorless oil in 76% yield.

| |
|---|
| IR($CHCl_3$)1765, 1735 $cm^{-1}$ |
| NMR($CDCl_3$, 90 MHz) |
| δ: 0.05(9H, s) |
| 0.8–1.1(2H, m) |
| 1.43(3H, s) |
| 1.60(3H, s) |
| 2.58(2H, m) |
| 3.31(1H, m) |
| 4.08–4.28(2H, m) |
| 4.36(1H, s) |
| 4.99(1H, d, J<2Hz) |
| 5.0–5.2(2H, m) |
| 5.5–6.1(1H, m) |

EXAMPLE 5

6-α-Allyl Penicillanic Acid Sodium Salt

Allyl 6-α-allyl penicillanate (300 mg) was dissolved in dry THF (3 ml) at r.t. under argon.

Sodium ethylhexanoate (185 mg) was added immediately followed by $PPh_3$ (15 mg) and tetrakis (triphenylphosphine) palladium (0) (15 mg).

The solution was stirred 1h at r.t.

After concentration of the solvent to a small volume, diethyl ether (12 ml) was added and the resulting mixture was stirred 10 minutes. The precipitate was isolated by centrifugation. The crude material was dissolved in a small amount of water and passed through a reverse-phase column (Merck LiChroprep C-18) eluting with distilled water, then with water-acetone acetone mixtures. The product containing fractions were freeze-dried to afford the title product as white powder (190 mg; 68%).

| |
|---|
| IR(KBr)1760, 1605 $cm^{-1}$ |
| NMR(200 MHz, $D_2O$) |
| δ: 1.50(3H, s) |
| 1.62(3H, s) |
| 2.55–2.64(2H, m) |
| 3.47(1H, m) |
| 4.25(1H, s) |
| 5.13(1H, d, J=1.5Hz) |
| 5.13–5.25(2H, m) |
| 5.96(1H, m) |

EXAMPLE 6 p-Nitrobenzyl 6-α-Allyl Penicillanate

A solution of allyl 6-α-allyl penicillanate (2.8 g) in dry THF (50 ml) was treated with sodium ethylhexanoate (1.7 g), PPh$_3$ (200 mg) and tetrakis (triphenylphosphine) palladium (0) (200 mg) and stirred 2h at r.t. under nitrogen. Solvent was removed under vacuum and the residue was dissolved in dry DMF (70 ml) and treated with p-nitrobenzylbromide (2.8 g). After stirring 2h at r.t. The reaction mixture was poured into ETOAc/icewater. The organic phase was dried and evaporated. Flash chromatography of the residue afforded the title product as a light yellow oil (3 g; 80% yield).

IR(CHCl$_3$)1775–1750 cm$^{-1}$
NMR(CDCl$_3$, 90 MHz)
δ:  1.45(3H, s)
    1.65(3H, s)
    2.62(2H, m)
    3.42(1H, m)
    4.54(1H, s)
    5.05(1H, d, J<2Hz)
    5.1–5.4(2H, m)
    5.29(2H, s)
    5.6–6.1(1H, m)
    7.24(2H, d, J=8.5Hz)
    8.27(2H, d, J=8.5Hz)

EXAMPLE 7 p-Nitrobenzyl 6-α-Formylmethylpenicillanate

A solution of p-nitrobenzyl 6-α-allyl penicillanate (3 g) in dichloromethane (140 ml) and 99% ETOH (70 ml) was cooled to −78° C. and ozonized until thin layer chromatography indicated complete consumption of starting material. Dimethylsulphide (4 ml) was added and the reaction mixture was allowed to warm to r.t. The solution was concentrated and the residue purified by flash-chromatography (eluting with n-hexane/ethyl acetate mixtures).

The title product was obtained as a foam (1.9 g).

IR(CHCl$_3$)1775, 1775, 1730 cm$^{-1}$
NMR(CDCl$_3$, 90 MHz)
δ:  1.42(3H, s)
    1.64(3H, s)
    3.03(2H, m)
    3.68(1H, m)
    4.53(1H, s)
    5.03(1H, d, J=1.6Hz)
    5.27(2H, s)
    7.55(2H, d, J=8.5Hz)
    8.25(2H, d, J=8.5Hz)
    9.82(1H, s)

EXAMPLE 8 p-Nitrobenzyl 6-α-(2-Hydroxyethyl)penicillanate

To a solution of p-nitrobenzyl 6-α-formylmethyl penicillanate (900 mg) in dry THF (60 ml), acetic acid (500 μl) and sodium-cyanoborohydride (1 g) were added.

The mixture was vigorously stirred for 30 minutes at room temperature, then concentrated under vacuum. The residue was taken-up with ethyl acetate and washed with water, 2N hydrochloric acid, 4% aqueous NaHCO$_3$ then water.

After drying over sodium sulphate the organic solvent was removed.

The title hydroxy compound was obtained in quantitative yield as a foam.

IR(CHCl$_3$)1745 (broad) cm$^{-1}$
NMR(CDCl$_3$, 90 MHz)
δ:  1.43(3H, s)
    1.63(3H, s)
    2.0–2.2(2H, m)
    3.45(1H, m)
    3.67–3.80(2H, m)
    4.52(1H, s)
    5.13(1H, d, J=1.6Hz)
    5.29(2H, s)
    7.58(2H, d, J=8Hz)
    8.25(2H, d, J=8Hz)

EXAMPLE 9 p-Methoxybenzyl 6-α-Propyl penicillanate

A solution of p-methoxybenzyl 6-α-allyl penicillanate (550 mg) in EtOAc (25 ml) and EtOH (25 ml) was treated with 5% Pd/C (200 mg) and hydrogenated at r.t. for 2h. Filtration of the catalyst and removal of the solvent gave the title product as a colorless oil in quantitative yield.

IR(CHCl$_3$)1765, 1750 cm$^{-1}$
NMR(CDCl$_3$, 90 MHz)
δ:  0.90(3H, t, J=7.0Hz)
    1.33(3H, s)
    1.56(3H, s)
    1.2–2.3(4H, m)
    3.23(1H, m)
    3.43(3H, s)
    4.41(1H, s)
    4.99(1H, d, J<2Hz)
    5.08(2H, s)
    6.85(2H, d, J=8.5Hz)
    7.28(2H, d, J=8.5Hz)

EXAMPLE 10 p-Methoxybenzyl 6-α-Propyl penicillanate 1,1-Dioxide

A solution of p-methoxybenzyl 6-α-propyl penicillanate (200 mg) in CHCl$_3$ (5 ml) was treated with 80% m.chloroperbenzoic acid (350 mg) and stirred five hours at r.t. The precipitate was filtered and the filtrate was washed with aqueous NaHSO$_3$ then with aqueous NaHCO$_3$. Removal of the solvent and flash chromatography of the residue gave the title product as a colorless oil (quantitative yield).

IR(CHCl$_3$)1795, 1750 cm$^{-1}$
NMR(CDCl$_3$, 90 MHz)
δ:  0.97(3H, t, J=7Hz)
    1.25(3H, s)
    1.52(3H, s)
    1.2–2.1(4H, m)
    3.68(1H, m)
    3.82(3H, s)
    4.30(1H, d, J<2Hz)
    4.35(1H, s)
    5.15(2H, ABq, J=11Hz)
    6.89(2H, d, J=8.5Hz)
    7.31(2H, d, J=8.5Hz)

EXAMPLE 11

6-α-Propyl penicillanic Acid 1,1 Dioxide Sodium Salt

A solution of p-methoxybenzyl 6-α-propyl penicillanate 1,1-dioxide (200 mg) in anisole (13 ml) and methylene chloride (1.5 ml) was cooled to −40° C.

Aluminum trichloride (300 mg) was added and the resulting mixture was stirred 1h at −40° C.

1M phosphate buffer (40 ml) and NaHCO$_3$ (1.2 g) were added and the mixture stirred 10 minutes at r.t. then filtered, washed with ethyl aetate and concentrated under vacuum. The residue in the minimum amount of water, was passed through a reverse-phase column (Merck LiChroprep C-18) eluting with water, then water-acetone mixtures.

The product containing factions were freeze-dried to afford the title product as a white powder (90 mg)
IR (KBr) 1760, 1615 cm$^{-1}$.

EXAMPLE 12

Methyl 6 α-Allyl Penicillanate 1,1-Dioxide

A solution of methyl 6-α-bromo penicillanate 1,1-dioxide (245 mg; 0.75 mmol), allyltributyltin (400 mg; 1.2 mmol) and azobisisobutyrronitrile (15 mg) in benzene (6 ml), was heated at reflux under argon for 5h. The cooled solution was passed through a short pad of silica gel (230–400 mesh) packed with n.hexane.

Eluting with n-hexane then n.hexane-ethyl acetate mixtures provided a white solid (200 mg; 93%) m.p. 93°-5°.

| | |
|---|---|
| | $α_D$ +169°(c 1.5 CHCl$_3$) |
| | IK(KBr)1800, 1750, 1640 cm$^{-1}$ |
| | MH$^{(+)}$ 288, (MH$^+$ —C$_5$H$_6$O)206 |
| | NMR(CDCl$_3$, 400 MHz) |
| δ: | 1.40(3H, s) |
| | 1.60(3H, s) |
| | 2.61-2.72(2H, m) |
| | 3.81(1H, m) |
| | 3.82(3H, s) |
| | 4.36(1H, d, J=1.8Hz) |
| | 4.39(1H, s) |
| | 5.18-5.23(2H, m) |
| | 5.78-5.85(1H, m) |

EXAMPLE 13

Allyl 6-α-Allyl Penicillanate 1,1-Dioxide

A solution of allyl 6-α-bromo penicillanate 1,1-dioxide (1.8 g), allyltributyltin (2.2 ml) and AIBN (50 mg) in benzene (20 ml) were refluxed under nitrogen for 8 h. The cooled solution was directly passed through a silica gel column packed with cyclohexane. Eluting with cyclohexane then with cyclohexane/EtOAc mixtures afforded a crude product which was freed from traces of tin derivatives by partitioning between n-hexane and acetonitrile. Acetonitrile was removed under vacuum affording the title allyl compound as a colorless oil (1.1 g; 69%).

| | |
|---|---|
| | $α_D$ +153°(c 1.2 CHCl$_3$) |
| | IR(CHCl$_3$)1800, 1755 cm$^{-1}$ |
| | NMR(CDCl$_3$ 90 MHz) |
| δ: | 1.37(3H, s) |
| | 1.58(3H, s) |
| | 2.63(2H, m) |
| | 3.75(1H, m) |
| | 4.32(1H, d, J<2Hz) |
| | 4.37(1H, s) |
| | 4.65(2H, d, J=7Hz) |
| | 5.0–5.5(4H, m) |
| | 5.6–6.1(2H, m) |

EXAMPLE 14 p-Methoxybenzyl 6-α-Allyl Penicillanate 1,1-Dioxide

Starting from p-methoxybenzyl 6-α-bromo penicillanate 1,1-dioxide and following the same methodology as described in Example 13.

The title product was obtained as colorless oil (76% yield).

| | |
|---|---|
| | IR(CHCl$_3$)1790, 1750 cm$^{-1}$ |
| | NMR(CDCl$_3$, 90 MHz) |
| δ: | 1.22(3H, s) |
| | 1.49(3H, s) |
| | 2.61(2H, m) |
| | 3.73(1H, m) |
| | 3.77(3H, s) |
| | 4.28(1H, d, J=2Hz) |
| | 4.32(1H, s) |
| | 5.12(2H, ABq, J=11Hz) |
| | 5.0–5.3(2H, m) |
| | 5.6–6.1(1H, m) |
| | 6.86(2H, d, J=8.5Hz) |
| | 7.28(2H, d, J=8.5Hz) |

EXAMPLE 15

6-α-Allyl penicillanic Acid 1,1-Dioxide Sodium Salt

Allyl 6-α-allyl penicillanate 1,1-dioxide (500 mg) was dissolved in dry THF (6 ml) at r.t. under argon.

Sodium ethylhexanoate (300 mg), triphenylphosphine (70 mg) and tetrakis (triphenylphosphine) palladium (0) (70 mg) were added sequentially. The solution was stirred 20 minutes at r.t. then diethyl ether (30 ml) was added.

The precipitate was isolated by centrifugation then dissolved in a small amount of water and passed through a reverse phase column (Merck Lichroprep C-18) eluting with water and water acetone mixtures. Fractions containing the product were pooled and freeze-dried to afford the title compound as a white powder (330 mg; 70%)
IR (KBr) 1760, 1610 cm$^{-1}$.

EXAMPLE 16

6-α-Allyl Penicillanic Acid 1,1-Dioxide Sodium Salt

Starting from p-methoxybenzyl 6-α-allyl penicillanate 1,1-dioxide and following the same procedure as described in EXAMPLE 11. The title product was obtained as white powder in 62% yield
IR (KBr) 1760, 1610 cm$^{-1}$.

EXAMPLE 17

Methyl 6-α-Allyl-6β-Bromo Penicillanate

Methyl 6,6-dibromo penicillanate (1.0 g) was dissolved in benzene (35 ml) then treated with allyltributyltin (1.0 g) and a catalytic amount of AIBN. The mixture was heated at reflux for 4h under argon, then concentrated under reduced pressure.

Flash chromatography over silica-gel (eluting with n-hexane then n-hexane - ethyl acetate) allowed the separation of three products. The faster running (TLC : n.hexane - ethyl acetate ¼) was shown to be methyl 6,6-diallylpenicillanate (103 mg; 13%). The second eluted product was unreacted starting material (260 mg; 26%).

The slower running fraction afforded the title compound as light yellow oil (474 mg; 53%)

| | |
|---|---|
| | $\alpha_D$ +211°(C 1.1 CHCl$_3$) |
| | IR(film)1790, 1750 cm$^{-1}$ |
| | NMR(400 MHz, CDCl$_3$) |
| δ: | 1.46(3H, s) |
| | 1.67(3H, s) |
| | 3.03(2H, m) |
| | 3.78(3H, s) |
| | 4.51(1H, s) |
| | 5.24–5.31(2H, m) |
| | 5.33(1H, s) |
| | 5.88(1H, m) |

EXAMPLE 18

Allyl 6-α-Allyl -6β-Bromo Penicillanate

Starting from allyl 6,6-dibromo penicillanate and following the same procedure as described in EXAMPLE 17, the title product was obtained as a colorless oil (55%).

| | |
|---|---|
| | $\alpha_D$ +194°(c 5.6 CHCl$_3$) |
| | IR(film)1790, 1745 cm$^{-1}$ |
| | NMR(400 MHz, CDCl$_3$) |
| δ: | 1.47(3H, s) |
| | 1.67(3H, s) |
| | 3.03(2H, m) |
| | 4.52(1H, s) |
| | 4.66(2H, m) |
| | 5.25–5.41(4H, m) |
| | 5.33(1H, s) |
| | 5.84–5.93(1H, m) |

EXAMPLE 19

Allyl 6-α-Allyl-6β-Bromo Penicillinate 1,1-Dioxide

Starting from allyl 6,6-dibromopenicillanate 1,1-dioxide and following the same procedure as described in EXAMPLE 17, the title product was obtained as yellowish oil (55%).

| | |
|---|---|
| | $\alpha_D$ +163°(c 1.0 CHCl$_3$) |
| | IR(CHCl$_3$)1810, 1755 cm$^{-1}$ |
| | NMR(90 MHz, CDCl$_3$) |
| δ: | 1.45(3H, s) |
| | 1.65(3H, s) |
| | 3.09(2H, d, J=7Hz) |
| | 4.52(1H, s) |
| | 4.53(1H, s) |
| | 4.72(2H, d, J=6Hz) |
| | 5.20–5.60(4H, m) |
| | 5.71–6.27(2H, m) |

EXAMPLE 20

Methyl 6β-Allyl Penicillanate

Tributyltinhydride (270 μl) was added to a solution of methyl 6-α-allyl -6β-bromopenicillanate (280 mg) in benzene (15 ml). The mixture was stirred 1h at r.t., then concentrated under vacuum. Chromatography on silica gel (n-hexane then n-hexane/ethyl acetate as eluants) afforded a colorless oil (185 mg).

| | |
|---|---|
| | $\alpha_D$ +304°(c 2.6 CHCl$_3$) |

| | |
|---|---|
| | IR(film)1780, 1755 cm$^{-1}$ |
| | NMR(400 MHz, CDCl$_3$) |
| δ: | 1.47(3H, s) |
| | 1.65(3H, s) |
| | 2.55(2H, m) |
| | 2.69(1H, m) |
| | 3.77(3H, s) |
| | 4.38(1H, s) |
| | 5.06–5.14(2H, m) |
| | 5.44(1H, d, J=4.5Hz) |
| | 5.76(1H, m) |

EXAMPLE 21

Allyl 6β-Allyl Penicillanate

Starting from allyl 6α-allyl-6β-bromo penicillinate and following the same procedure as described in EXAMPLE 20, a colorless oil, corresponding to the title product, was obtained in 83% yield.

| | |
|---|---|
| | $\alpha_D$ +286°(c 5.0 CHCl$_3$) |
| | IR(film)1755, 1745 cm$^{-1}$ |
| | NMR(400 MHz, CDCl$_3$) |
| δ: | 1.48(3H, s) |
| | 1.65(3H, s) |
| | 2.54(2H, m) |
| | 3.69(1H, dt, J=4.3 and 7.2Hz) |
| | 4.38(1H, s) |
| | 4.66(2H, m) |
| | 5.06–5.13(2H, m) |
| | 5.29(1H, dd, J=1.1 and 10.3Hz) |
| | 5.37(1H, dd, J=1.3 and 17.2Hz) |
| | 5.43(1H, d, J=4.3Hz) |
| | 5.74–5.81(1H, m) |
| | 5.88–5.96(1H, m) |

EXAMPLE 22

Allyl 6β-Allyl Penicillanate 1,1-Dioxide

Starting from allyl 6α-allyl-6β-bromo penicillanate 1,1-dioxide, and following the procedure described in EXAMPLE 20, the title product was obtained as colorless oil (88%).

| | |
|---|---|
| | $\alpha_D$ +192°(c 1.0 CHCl$_3$) |
| | IR(CHCl$_3$)1810, 1755 cm$^{-1}$ |
| | NMR(90 MHz, CDCl$_3$) |
| δ: | 1.43(3H, s) |
| | 1.62(3H, s) |
| | 2.5–3.3(2H, m) |
| | 3.92(1H, m) |
| | 4.48(1H, s) |
| | 4.63(1H, d, J=4.5Hz) |
| | 4.71(2H, d, J=6Hz) |
| | 5.1–5.6(4H, m) |
| | 5.65–6.25(2H, m) |

EXAMPLE 23

6β-Allyl Penicillanic Acid Sodium Salt

Allyl 6β-allyl penicillanate (2.0 g) was dissolved in dry THF (20 ml) at r.t.

Sodium ethyl hexanoate (1.25 g), triphenylphosphine (400 mg) and tetrakis (triphenylphosphine) palladium (0) (60 mg) were added sequentially. The solution was stirred 35 minutes at r.t., then diethyl ether (200 ml) was added. The precipitate, collected by centrifugation, was dissolved in a small amount of water and passed through a reverse phase column (Merck LiChroprep C-18) eluting with water and water/acetonitrile mixtures.

The product-containing fractions were pooled and freeze-dried to afford the title product as a white powder (1.48 g).
IR (KBr) 1760, 1610 cm$^{-1}$.

EXAMPLE 24

6β-Allyl Penicillanic Acid 1,1-Dioxide Sodium Salt

Starting from allyl 6β-allyl penicillanate 1,1-dioxide and following the same procedure as described in EXAMPLE 23, the title product was obtained in 54% as white powder.

| | |
|---|---|
| | IR(KBr)1770, 1750, 1605 cm$^{-1}$ |
| | NMR(200 MHz, D$_2$O) |
| δ: | 1.41(3H, s) |
| | 1.54(3H, s) |
| | 2.50–2.96(2H, m) |
| | 4.21(1H, m) |
| | 4.26(1H, s) |
| | 5.07(1H, d, J=4.1Hz) |
| | 5.14–5.26(2H, m) |
| | 5.92(1H, m) |

PROCEDURE A p.Methoxybenzyl 6,6-Dibromo Penicillanate 1,1-Dioxide

A solution of 6,6-dibromopenicillanic acid 1,1-dioxide (47 g) in dry DMF (220 ml) was treated with triethylamine (26.4 ml) at 0° C.

p.Methoxybenzylchloride (27.8 ml) and sodium iodide (20 g) were added and the resulting mixture was stirred overnight. The slurry was slowly poured onto ice-water under vigorous stirring. The precipitate was filtered, washed with water then dried in vacuo.

Crystallization from methanol gave white crystals (49 g; 85%). m.p. 130°–131°.

| | |
|---|---|
| | IR(KBr)1815, 1745 cm$^{-1}$ |
| | NMR(CDCl$_3$, 90 MHz) |
| δ: | 1.19(3H, s) |
| | 1.51(3H, s) |
| | 3.78(3H, s) |
| | 4.46(1H, s) |
| | 4.94(1H, s) |
| | 5.16(2H, ABq, J=10Hz) |
| | 6.87(2H, d, J=8.5Hz) |
| | 7.28(2H, d, J=8.5Hz) |

PROCEDURE B

Allyl 6,6-Dibromo Penicillanate 1,1-Dioxide 6,6-Dibromopenicillanic acid 1,1-dioxide (15.6 g) was dissolved in DMF (150 ml) and treated with triethylamine (7 ml) and allyl bromide (4.3 ml).

The resulting mixture was stirred for 4h at r.t., then poured into EtOAc/ice-water. The organic phase was washed twice with water then dried and concentrated. The residue was crystallized from diisopropylether-n-hexane to afford the title product as white crystals (13 g; 76%).

| | |
|---|---|
| | α$_D$ +172°(c 4.9 CHCl$_3$) |
| | m.p. 80–82° |
| | IR(KBr)1810, 1755 cm$^{-1}$ |
| | NMR(CDCl$_3$, 400 MHz) |
| δ: | 1.42(3H, s) |
| | 1.63(3H, s) |
| | 4.53(1H, s) |
| | 4.72(2H, m) |
| | 5.02(1H, s) |
| | 5.35(1H, dd, J=0.8 and 10.3Hz) |
| | 5.41(1H, dd J=1.3 and 16.9Hz) |
| | 5.89–5.96(1H, m) |

PROCEDURE C

Allyl 6-α-bromo penicillanate 1,1-Dioxide

A solution of allyl 6,6-dibromopenicillanate 1,1-dioxide (2.6 g; 6.03 mmol) in dry THF (100 ml) was cooled to −78° C. 2M Ethyl magnesium bromide in either (2M solution, 3.05 ml=6.1 mmol) was added dropwise in five minutes. After stirring for 10 min., saturated aq.NH$_4$Cl was dropped (10 ml). The resulting mixture was partitioned between ether and sat.aq.NH$_4$Cl. After drying over MgSO$_4$, removal of the solvent gave a light yellow oil (2.0 g; 94%) which solidified on standing.

| | |
|---|---|
| | α$_D$ +162°(c 1.8, CHCl$_3$) |
| | IR(KBr)1800, 1755 |
| | NMR(CDCl$_3$, 400 MHz) |
| δ: | 1.43(3H, s) |
| | 1.63(3H, s) |
| | 4.44(1H, s) |
| | 4.70(1H, d, J=1.3Hz) |
| | 4.71(2H, m) |
| | 5.16(1H, d, J=1.3Hz) |
| | 5.35(1H, dd, J=0.9 and 10.4Hz) |
| | 5.40(1H, dd, J=1.1 and 17.1Hz) |
| | 5.85–5.97(1H, m) |

PROCEDURE D p-Methoxybenzyl 6-α-Bromo Penicillanate 1,1-Dioxide

Following the same methodology as described in PROCEDURE C and starting from p-methoxybenzyl 6,6-dibromo penicillanate 1,1-dioxide, the title compound was obtained in 83% yield. (White crystals m.p. 81°–83°).

| | |
|---|---|
| | IR(KBr)1805, 1750 cm$^{-1}$ |
| | NMR(CDCl$_3$, 90 MHz) |
| δ: | 1.23(3H, s) |
| | 1.52(3H, s) |
| | 3.78(3H, s) |
| | 4.39(1H, s) |
| | 4.66(1H, d, J<2Hz) |
| | 5.15(2H, s) |
| | 5.18(1H, d, J<2Hz) |
| | 6.87(2H, d, J=8.5Hz) |
| | 7.31(2H, d, J=8.5Hz) |

Having now fully described the present invention, it will be apparent to one skilled in the art that many changes and modifications can be made thereto without departing from the spirit or scope of the invention as set forth herein.

What is claimed as new and desired to be secured by letters patent of the United States is:

1. A method of inhibiting the action of β-lactamase enzymes in an individual in need of such inhibition treatment, which comprises treating said individual with an effective amount of 6β-allyl penicillanic acid 1,1-dioxide or its pharmaceutically or veterinarily acceptable salts.

2. The method of claim 1, wherein 6β-allyl penicillanic acid 1,1-dioxide sodium salt is employed for treating said individual.

3. The method of claim 1, wherein the treatment of said individual is carried out with a mixture of 10 to 90% by weight of the mixture of 6β-allyl penicillanic acid 1,1-dioxide or it pharmaceutically or veterinarily acceptable salts with a β-lactam antibiotic susceptible to destruction by β-lactamase.

* * * * *

UNITED STATES PATENT AND TRADEMARK OFFICE
CERTIFICATE OF CORRECTION

PATENT NO. : 5,200,403
DATED : April 6, 1993
INVENTOR(S) : Marco Alpegiani et al.

It is certified that error appears in the above-identified patent and that said Letters Patent is hereby corrected as shown below:

On the title page, Item [30],

The Foreign Application Priority Data has been omitted, should read as follows: --July 10, 1987 [GB] Great Britian......8716300--

Signed and Sealed this

Thirtieth Day of November, 1993

Attest:

BRUCE LEHMAN

Attesting Officer

Commissioner of Patents and Trademarks